| United States Patent [19] | [11] Patent Number: 4,966,993 |
| Turbanti et al. | [45] Date of Patent: Oct. 30, 1990 |

[54] PROCESS FOR PREPARATION OF 3-HYDROXY-3-METHYL-GLUTARIC ACID

[75] Inventors: Luigi Turbanti, Pisa; Giorgio Garzelli, Leghorn, both of Italy

[73] Assignee: Laboratori Guidotti SpA, Pisa, Italy

[21] Appl. No.: 338,406

[22] Filed: Apr. 12, 1989

Related U.S. Application Data

[63] Continuation of Ser. No. 133,198, Dec. 15, 1987, abandoned, which is a continuation-in-part of Ser. No. 792,446, Oct. 29, 1985, abandoned.

[30] Foreign Application Priority Data

Oct. 29, 1984 [IT] Italy ................................ 23360 A/84

[51] Int. Cl.$^5$ .............................................. C07C 51/27
[52] U.S. Cl. ................................... 562/540; 560/182; 562/580; 562/582
[58] Field of Search ................. 562/582, 540; 560/182

[56] References Cited

U.S. PATENT DOCUMENTS

| 2,867,657 | 1/1959 | Selwitz | 562/540 X |
| 3,818,080 | 6/1974 | Baran et al. | 562/538 X |
| 4,433,163 | 2/1984 | Lehky | 562/204 |
| 4,546,203 | 10/1985 | Metzner | 562/538 |

OTHER PUBLICATIONS

*The Merck Index*, 9th Ed; Merck and Co; Rahway, New Jersey; Entries 6393 amd 6395; p. 854, (1976).

*Primary Examiner*—Werren B. Lone
*Assistant Examiner*—Vera C. Clarke
*Attorney, Agent, or Firm*—McAulay Fisher Nissen & Goldberg

[57] ABSTRACT

For the preparation of 3-hydroxy-3-methyl-glutaric acid a process is disclosed based on the direct oxidation with nitric acid of 3-methyl-1,3,5-pentanetriol.

4 Claims, No Drawings

PROCESS FOR PREPARATION OF 3-HYDROXY-3-METHYL-GLUTARIC ACID

This is a continuation of application Ser. No. 133,198, filed Dec. 15, 1987, now abandoned, which in turn is a continuation-in-part of application Ser. No. 792,446, filed Oct. 29, 1985, now abandoned.

The present invention relates to the preparation of 3-hydroxy-3-methyl-glutaric acid, having the formula:

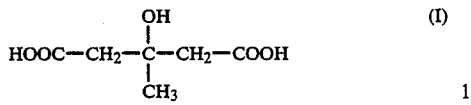

and more specifically to an improved process for such a preparation. The 3-hydroxy-3-methyl-glutaric acid (meglutal) is a compound present in the human organism and appears among the products of the endogenetic synthesis of cholesterol; it is endowed with hypolipidemic and hypocholesterolemic properties which are well known in therapy and related to its properties of reducing, if administered at suitable dosages, the cholesterol synthesis.

This compound is prepared by synthesis according to several methods which can be grouped in few fundamental synthesis schemes.

(A) Oxidation with ozone and hydrogen peroxide of diallyl-methylcarbinol, which is in turn prepared by the use of the Grignard reactant, allylmagnesiumbromide (J. AM. Chem. Soc., 76, 1289, 1954) followed by oxidation of this intermediate with alkali permanganates (Belgian Patent 872.650 of Jan. 30, 1979).

(B) Reaction according to Reformatsky between ethylbromoacetate and ethylacetoacetate (J. AM. CHEM. Soc. 53, 18433, 1931; idem 75, 2377, 1935), or reaction between alkali-metal derivatives of alkylacetates and acetylhalides (European Application No. 97.578 of Jan. 4, 1984), followed by saponification of the ethyl diester.

(C) Hydrolysis with alkali and hydrogen peroxide of glutaronitrile, which in turn can be obtained from 1-chloro-2,3-epoxy-2-methylpropane and potassium cyanide (Synthesis 1981, 791).

To the above essential synthesis processes involving several steps, some of which are also difficult or dangerous for the industrial practicing, recently a new process has been added consisting in the permanganic oxidation of an intermediate, 3-methyl-1,3,5-pentanetriol, this product being actually available on the market (European Patent Application No. 82344 of June 29, 1983).

This process, by which meglutol is directly prepared in one step only, is consequently potentially advantageous, mainly from the industrial point of view, with respect to the previous processes. The advantages of this process have been confirmed by the laboratory experimental work, but its practicing in equipments of the industrial type raises problems and is not satisfactory as regards the results, mainly owing, to the big amount of inorganic salts which are present in the reaction product, whereby two types of problems exist: the particular physical appearance of the reaction residue which, owing to its glass consistency, can not be solubilized in the solvents used for the normal handling and equipments used in the industrial production; the presence in the raw reaction product of high amounts of inorganic salts which can not be completely removed by crystallization without reducing also the final yield of meglutol, owing to its hydrophylic properties.

These drawbacks have been overcome with the new oxidation method of 3-methyl-1,3,5-pentanetriol by which meglutol can be provided which is devoid of inorganic substances and consequently more adapted for the practicing in industrial plants.

The present invention thus relates to a synthesis process for the 3-hydroxy-3-methyl-glutaric acid consisting in the oxidation with nitric acid, according to the following scheme 1, of 3-methyl-1,3,5-pentanetriol, an intermediate which is simple and readily practiceable in all its steps in the industrial plants and consequently characterized, with respect to the known processes, by the economicity and industrial feasibility.

SCHEME 1

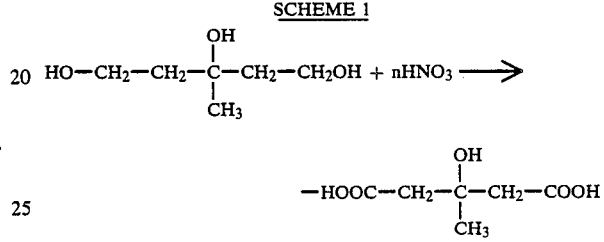

More particularly the present process is advantageously distinguished also with respect to the process disclosed in the European Application 82344 since the use of nitric acid in the oxidation of 3-methyl-1,3,5-pentanetriol causes the above mentioned drawbacks which were faced in the industrial practicing with alkali permanganate, to be done away with giving place also to other positive results; more detailedly the advantages found with the use of nitric acid are the following:

1. The absence of inorganic substances in the reaction product first of all makes the process readily practiceable in the industrial plants and permit meglutol to be obtained with high purity through crystallization from alkyl acetate, whereby also the use of acetonitrile is avoided which, owing to its toxicity and dangerousness, involves particular expedients to be fulfilled.

2. The yields of meglutol, according to the present process, are higher than 60% with respect to the theoretical yield, in comparison with the 40% which can be obtained with permanganate: such a result in combination with the different price of the two oxidizing agents, causes the price of the meglutol obtained with the present process (as calculated from the raw materials only) to be sensibly reduced, it being equal to 50% of that prepared with permanganate.

3. By the process with nitric acid the volumes of reaction solvents are caused to be reduced from 4 liters/kg of obtained meglutol to 8 liters/kg, and the filtration of relevant amounts of manganese dioxide (3.8 kg/kg meglutol) is eliminated, this operation requiring, as it is known, not negligible times, whereby also a reduction of the labour costs involved in the final product is obtained.

The process according to the invention consists in slowly adding 3-methyl-1,3,5-pentanetriol to an excess of nitric acid having a density of between 1.20 and 1.50, at a rate such that, possibly with simultaneous cooling, the temperature of the reaction mixture is maintained below 35° C., the reaction being thereafter brought to completion within 2–6 hours at temperature of between 20°–80° C. Differently from the results reffered to in the chemical literature as regards the oxidation reactions carried out nitric acid, in the present case if nitric acid would be used having a density lower than 1.20, meglutol would be still formed but in very yield low and accompanied by several byproducts, whereas the optimum results have been obtained with nitric acid having a density higher than 1.20, preferably of 1.35, leaving the reaction to proceed at about 30° C. for 2–3 hours and then carrying out a final heating for about half an hour at a temperature of between 40° and 60° C.

The reaction solution is thereafter distilled under vacuum at a temperature lower than 60° C., part of the unreacted nitric acid being recovered, and a residue is obtained in form of a pale yellow oil which is dissolved, without difficulty, in hot butyl acetate and gives by cooling 3-hydroxy-3-methyl-glutaric acid having a title of 98% and with a yield of about 75%.

This product can be furthermore crystallized from alkyl acetates, dialkylketones or alcohols, giving place, with a yield higher than 80%, a product having a title of about 99.5%.

The invention is more detailedly illustrated in the following example.

EXAMPLE

In a 1000 ml flask 880 g (10 mol) of concentrated nitric acid (71.6%; D=1.42) are charged, by controlling that its temperature is not lower than 25° C., and under stirring a small portion of 3-methyl-1,3,5-pentanetriol is added, than awaiting the development of nitrogen tetroxide and the temperature raising, these phenomena indicating that the reaction has been started; then, by externally cooling with icy water, the remaining 3-methyl-1,3,5-pentanetriol is added, for a total amount of 142 g, at a rate such that the reaction temperature is maintained in the range of 25°–35° C., over about 2 hours.

Then the reaction is left to proceed to completion, the brown solution being maintained for further two hours at 25°–35° C. and for half an hour at 50°–55° C.

The final pale yellow solution is evaporated under vacuum at a temperature lower than 50° C., giving 210 grams of a yellowish oil, which is dissolved in the same flask in 600 ml of butyl acetate, the resulting solution is added with carbon, hot filtered and distilled under vacuum at a temperature less than 60° C., until 100 ml of distillate are collected: the remaining solution is cooled and there is immediately formed a colourless crystalline precipitate which is filtered at the temperature of 10° C. and dried in an oven under vacuum giving 114 g of 3-hydroxy-3-methyl-glutaric acid having a title of 98%. The yield is about 75%. A further crystallization from butyl acetate gives 97 g (yield 85%) of 3-hydroxy-3-methyl-glutaric acid with a title higher than 99.5%.

We claim:

1. A process for the preparation of 3-hydroxy-3-methyl-glutaric acid having the formula:

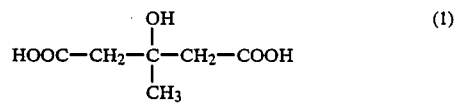

and which is devoid of inorganic substances, comprising, in combination:
  slowly adding a small portion of 3-methyl-1,3,5-pentanetriol to an excess of nitric acid having a density of between 1.20 and 1.50 at a temperature not lower than 25° C. to form a reaction solution;
  awaiting development of nitrogen tetroxide and an increase in temperature to indicate that the reaction has started;
  adding the remaining 3-methyl-1,3,5-pentanetriol to said solution over a period of about 2 hours and simultaneously cooling the reaction mixture to maintain the reaction mixture at a temperature of from 25° to 35° C.;
  allowing the reaction to complete at about 25° to 35° C. for about two hours and at about 50° to 55° C. for about half an hour;
  evaporating the resulting solution under vacuum at a temperature below 50° C. and dissolving the resulting oily residue in a solvent and distilling the resulting solution under vacuum and cooling the residue of said distilling to form the desired product.

2. The process of claim 1, wherein said product is obtained as an oily residue, dissolved in hot butyl acetate and cooled.

3. The process of claim 2, wherein said cooled product is crystallized from alkyl acetates, dialkyl ketones or alcohols.

4. The process according to claim 1, wherein the molar ratio of nitric acid to triol is between 3:1 and 12:1.

* * * * *